United States Patent [19]

Heyman et al.

[11] Patent Number: 5,085,073
[45] Date of Patent: Feb. 4, 1992

[54] THERMAL REMOTE ANEMOMETER SYSTEM

[75] Inventors: Joseph S. Heyman, Williamsburg; D. Michele Heath, Newport News; Christopher S. Welch, Gloucester; William P. Winfree, Williamsburg; William E. Miller, Hampton, all of Va.

[73] Assignee: The United States of America as represented by the Administrator of the United States National Aeronautics and Space Administration, Washington, D.C.

[21] Appl. No.: 146,939

[22] Filed: Jan. 22, 1988

[51] Int. Cl.$^5$ .................................................. G01F 9/00
[52] U.S. Cl. ..................................... 73/147; 374/124; 374/135; 73/204.11
[58] Field of Search ............. 73/204, 147, 204.23, 73/204.11, 204.24, 204.25; 374/5, 7, 54, 121, 124, 135, 130, 131, 132, 29, 30

[56] References Cited

U.S. PATENT DOCUMENTS

| | | | |
|---|---|---|---|
| 3,632,212 | 1/1972 | Bernal | 356/45 |
| 3,635,085 | 1/1972 | Shimotsuma et al. | 374/130 |
| 3,672,221 | 6/1972 | Weil | 73/339 R |
| 3,977,244 | 8/1976 | Stone | 73/147 |
| 4,075,493 | 2/1978 | Wickersheim | 250/461 R |
| 4,215,275 | 7/1980 | Wickersheim | 250/459 |
| 4,223,226 | 9/1980 | Quick et al. | 250/458 |
| 4,231,248 | 11/1980 | Rolinski et al. | 73/15.6 |
| 4,262,198 | 4/1981 | Gupta et al. | 250/340 |
| 4,433,329 | 2/1984 | Streib | 374/30 |
| 4,448,547 | 5/1984 | Wickersheim | 374/131 |
| 4,557,607 | 12/1985 | Busse | 374/130 |
| 4,621,929 | 11/1986 | Phillips | 374/131 |
| 4,654,803 | 3/1987 | Sell | 73/204 |

FOREIGN PATENT DOCUMENTS 0625162 9/1978 U.S.S.R. ..................... 73/204.24

*Primary Examiner*—Herbert Goldstein
*Attorney, Agent, or Firm*—Kevin B. Osborne

[57] ABSTRACT

A sample in a wind tunnel is radiated from a thermal energy source exteriorly of the wind tunnel. A thermal imager system, also located exteriorly of the wind tunnel, reads surface radiations from the sample as a function of time. The produced thermal images are characteristic of the heat transferred from the sample to the flow across the sample. In turn, the measured rates of heat loss of the sample are characteristic of the flow and the sample.

21 Claims, 1 Drawing Sheet

THERMAL REMOTE ANEMOMETER SYSTEM

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

1. Field of the Invention

The present invention relates generally to anemometers and, more specifically, to a thermal remote anemometer system.

2. Description of Related Art

Wind tunnel testing has become increasingly more important over the years. The increase in such testing has brought an increasing need to control and measure the flow characteristics of the tunnels and models. For example, the flow may need to be altered to minimize shock waves; or the flow may need to be reduced from a supersonic mode to a subsonic mode. To be able to provide specific characterization to the flow, it is necessary to have the ability to accurately measure the flow characteristics.

In the past, gas flow characterization has been accomplished by mechanical and thermal devices. One typical mechanical device is a rotating anemometer such as a wind cup or windmill device that relates its rotational speed to the flow. One drawback to these devices is that they only measure a swept volume which may not necessarily be clearly indicative of the flow adjacent a test model. Other drawbacks are their flow speed limitations and size restrictions.

Thermal anemometer devices have included the hot-wire type. Those hot-wire devices supply a measured current to the tip of the sensor. A change in current is a measure of the heat transferred away from the sensor, which is an indication of the flow over the sensor. Some problems associated with the hot-wire type device are that holes may have to be drilled in the test models, wires must be run internally of the model and brought out of a wind tunnel for measurement, and the model must be refinished to remove artifacts. If the model is not properly refinished, artifacts may interact with the flow and thereby affect the reliability of the measurements. The point measurements provided by hot-wire devices are also undesirable due to their fixed location and inability to scan.

Artisans have attempted to provide remote measurement devices, but these typically only measure temperature of an object rather than providing characteristics of a flow around a model. These are found, for example, in Wickersheim, "Optical Temperature Measurement Technique Utilizing Phosphors," U.S. Pat. No. 4,075,493; Quick et al., "Fiber Optic Temperature Sensor," U.S. Pat. No. 4,223,226; and Bernal, "Gas Temperature Measurement System Employing A Laser," U.S. Pat. No. 3,632,212.

A need still exists in the art to provide an anemometer system that can accurately characterize a flow over a model, such as one in a wind tunnel, in a remote, non-contact and passive fashion.

SUMMARY OF THE INVENTION

An object of the invention is to provide an improved remote, non-contact, thermal anemometer system.

Another object of the present invention is to provide a thermal anemometer system that is passive so that the measured sample or model does not act as its own thermal source for measurement.

A further object of the present invention is to provide an anemometer system that measures the heat loss of a model to determine the characteristics of a flow over the model.

An additional object of the present invention is to provide an anemometer system that can characterize a flow at various measurement areas on a model.

An even further object of the present invention is to provide a measurement system for flow characteristics which is not highly sensitive to variations in the absorption or emissivity of a material out of which a model is constructed.

The objects of the present invention are particularly accomplished by non-invasively imparting thermal energy to a sample in the wind tunnel. A plurality of surface radiations from the sample is received and then integrated. A change in surface radiations is then measured and compared with a reference characterization.

These and other objects of the present invention can best be seen from examination of the specifications, claims, and drawings.

DESCRIPTION OF THE PREFERRED EMBODIMENTS

The following description is provided to enable any person skilled in the electrical and gas dynamics fields to make and use the present invention and sets forth the best mode contemplated by the inventors of carrying out their invention. Various modifications, however, will remain readily apparent to those skilled in the arts, since the generic principles of the present invention have been defined herein specifically to provide a thermal remote anemometer system. Furthermore, while the following description is provided in the context of a wind tunnel, artisans should understand that the present invention can be applied in other contexts.

Figure 1:
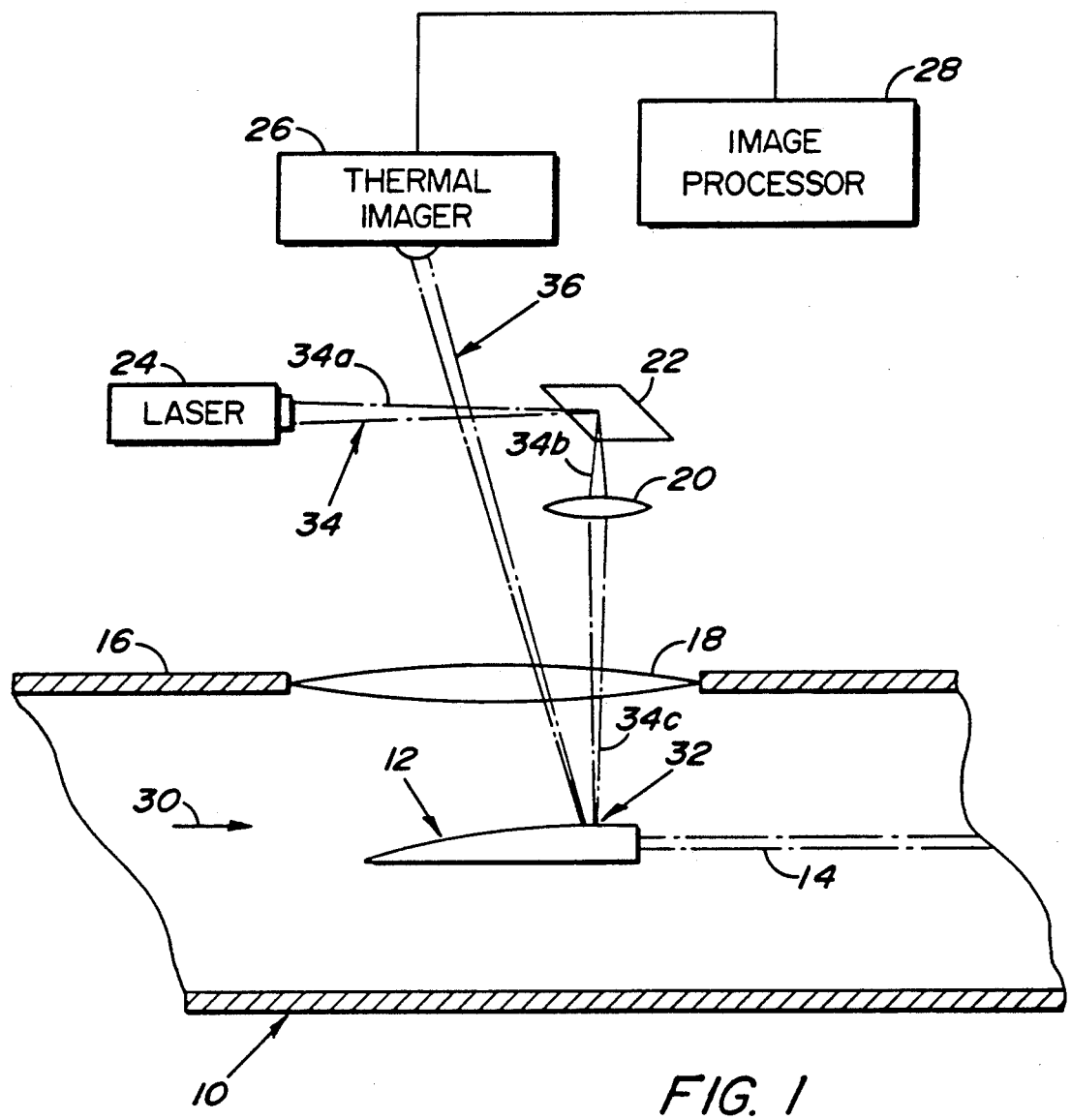
FIG. 1 illustrates one embodiment of the present invention.

In FIG. 1, a wind tunnel 10 is depicted. A flow 30 passes through the tunnel 10 in the direction shown by the arrow. A model or sample 12 is fixed within the wind tunnel 10 by a conventional sting element 14 or any other appropriate conventional design to fix the model 12 in the wind tunnel 10 for testing.

The wind tunnel 10 is enclosed by a conventional sidewall 16. A window element 18 is fixed in the sidewall 16 to provide operative thermal communication between the sample 12 and the environment exteriorly of the wind tunnel 10. In this particular embodiment, the window element 18 is constructed of an infrared transparent material to enable infrared energy to be imparted onto the sample 12, as further described below.

A thermal energy source 24 is provided exteriorly of the tunnel 10 and produces thermal energy which can be directed onto the sample 12. In this particular embodiment, the energy source 24 is a laser that operates in a pulse mode. The laser 24 produces an imparting energy beam that propagates through an input path 34 to the sample 12. Prior to impinging upon the sample 12, the imparting beam travels along a portion 34a of the input path 34 and into a conventionally designed scanning system 22 that scans the laser beam in two orthogonal angles to permit scanning over the sample surface. The scanning system 22 also integrates the scan to determine the total energy in the imparting beam to remove power fluctuations in the source 24. The scanning system 22 additionally directs the laser beam along a portion 34b of the input path 34 and into a conventionally designed focusing system 20. The focusing system 20 focuses the laser beam along a portion 34c of the input path 34. The focused laser beam then impinges upon a measurement area 32 of the sample 12.

The measurement area 32 is described by a portion of the surface area of the model 12. While FIG. 1 depicts only one measurement area 32, the present invention contemplates the use of a plurality of measurement areas 32, as more fully described below. In that fashion, one may obtain a temperature image over the entire model 12. In addition, one may rapidly scan the beam 34 to create a line of heat instead of a spot 32, and thus be sensitive to a vector flow of heat away from the line.

In one particular embodiment of the present invention, the surface of the model 12 does not require a surface coating to absorb thermal energy from the laser 24. Instead, the model 12 remains unaltered, which thereby enables multiple testing of the model 12 without the need to remove a coating upon subsequent tests or apply a coating for other tests.

Nevertheless, the present invention further contemplates that the model 12 can be coated with a thermal insulator coating and a surface absorbing coating. The thermal insulator coating minimizes the thermal energy transferred from the coating to the model body, thus optimizing heat into the flow. The surface absorbing coating tends to keep the thermal energy at the surface of the model 12 where it can interact with the flow 30 in the fashion described below. Such coatings may, for example, be needed when the model 12 has relatively high diffusivity characteristics.

The thermal insulator coating may be made of a compound such as a plastic, while the absorbing coating may be made of a compound such as black paint. Preferably, the thermal insulator coating and the surface absorbing coating are thin enough so that the aerodynamics of the model 12 are not changed. However, as the surface coatings become thinner, the temperature measurements described below must be accomplished faster. This is necessary to minimize heat transfer to the bulk material of the model 12, which transfer affects the signal-to-noise ratio of the temperature measurements.

A conventionally designed thermal imager system 26 is provided exteriorly of the wind tunnel 10 and receives surface radiations from the model 12. The surface radiations travel from the model 12, along an output path 36, and to the imager system 26. In this embodiment wherein the energy source 24 provides a pulsed imparting energy beam, the imager system 26 scans the surface radiations from the measurement area 32 following the pulse of imparting radiation. The surface radiations or the surface temperature of the model 12 depends on the energy absorbed, the thermal properties of the model (i.e., specific heat and diffusivity), the time separation between the laser pulse and the thermal measurement, and the heat transferred to the surrounding flow 30.

The thermal imager system 26 measures the surface radiations from the measurement area 32 over time (FIG. 1). The imaging system also determines the surface radiations without a flow to provide a measurement of total heat transferred to the model, which serves as a baseline for calibration. Thereby, the imager system can measure the rate of change in total radiation to provide signals or thermal images of the flow 30 as a function of time. The thermal images produced are characteristic of the flow 30 because the rate of change in heat is indicative of the heat loss to the flow 30. The rate of change increases as the flow 30 increases in velocity and decreases as the flow 30 decreases in velocity. The rate is furthermore influenced by the quality of the flow, such as laminar or turbulent flow. The rate of change can also be measured at a plurality of measurement areas 32 and thereby provide a flow image over the entire model 12.

A conventionally designed image processor system 28 is provided exteriorly of the tunnel 10. The processor system 28 takes the thermal image or temperature distribution curve (as a function of time) produced by the imager system 26 and performs a curve-fitting function on it of temperature versus time to determine heat transfer. Measurements with and without flow are subtracted to determine flow. The curve-fitting function improves the signal-to-noise ratio proportionately by the square root of the number of relevant data points. The temperature fit is then compared to a reference characterization or thermal theoretical model, such as a line with a Gaussian cross-section or Laplace's solution for evolution of a line with an arbitrary initial cross-section. Such comparison provides a determination of the flow 30 characteristics with respect to heat transferred from the model 12 to the flow 30.

In an alternative embodiment of the present invention, rather than a pulsed beam from the laser 24, a continuous beam is utilized. In such a case, there is no inherent time separation between imparting the beam and reading the resulting surface radiations, as with a pulsed laser. If there is no effective spacial separation between the two steps, the thermal measurements in the input path 34 and the output path 36 overlap and thus provide a poor signal-to-noise ratio. Therefore, the continuous beam is made invisible to the imager system 26, for example, by using an optical frequency that cannot be read by the imager system 26 or by spacially separating an area that is radiated by the laser (heating) from an area through which the imager system 26 obtains measurement data (cooling). Separating those two areas also enables the input path 34 to be spacially offset from the output path 36 while the scanning occurs.

As in the first embodiment above, the extent to which the sample 12 is radiated depends on the sample's innate thermal properties, the power of the continuous beam, and the dwell time of the beam. The imager system 26 scans the sample 12 for a fixed period of time after the sample 12 has been radiated by the continuous beam. As above, the measured rate of heat loss can then be related to the flow 30.

In another embodiment of the present invention, the laser 24 provides a modulated amplitude or frequency beam, depending on the optical absorption of the model. The imager system 26 scans the produced thermal image to conventionally extract the thermal phase and amplitude characteristics from the imparting beam to improve the signal-to-noise ratio.

Figure 2:
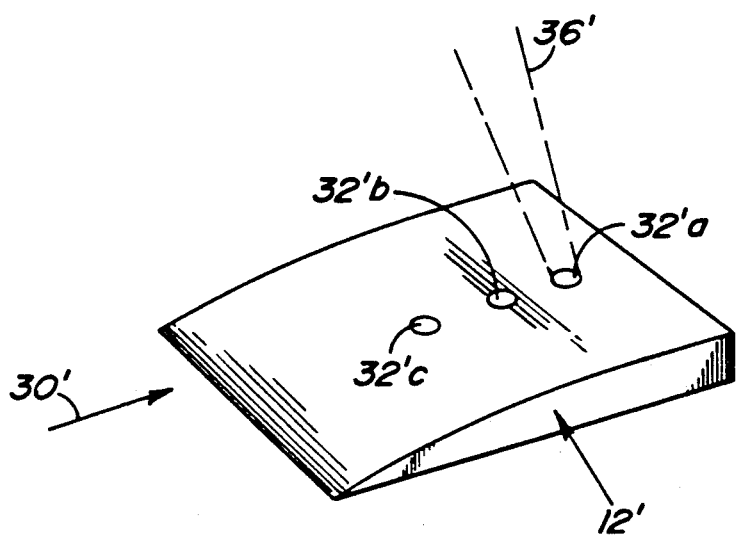
FIG. 2 partially illustrates another embodiment of the present invention wherein a thermal pattern is produced on a model.

In contrast to a single discrete measurement area 32, the laser beam can be scanned to produce a thermal pattern such as a line, a series of spots, or a grid. FIG. 2 depicts a thermal pattern of spots for illustration purposes, although other patterns and configurations are contemplated. In FIG. 2, a model 12' includes three measurement area 32'a, b, c. A flow 30' moves toward the model 12' and across the three radiated measurement areas. Each measurement area produces thermal radiations that propagate along a respective output path 36' (only one of which is shown). The imager system then simultaneously reads the surface radiations through each output path 36'. In so doing, the imager system provides data from a plurality of areas of the model 12' and thereby characteristics of the flow 30' at various parts of the model 12'.

Another thermal pattern is a line which can improve vector detection of the flow 30. Difference measurements of thermal transfer to the flow are taken between orthogonal heating lines intersecting at the measurement area by scanning the laser in orthogonal line directions by the scanning system 22.

The thermal pattern can also be varied in both time and space to determine, for example, sample thickness. Such a determination could include a relatively short laser pulse which enables a peak temperature decay to be examined. If one knows the thermal properties of the model material, and loss to the flow, then the decay is related to the model thickness.

The invention also has application for characterizing the properties of the model 12 itself. For example, if a crack exists in the model 12, the thermal image produced at the crack will be different from the non-cracked area of the model 12. This is due to the change in heat transfer of the model 12 from the change in geometry caused by the crack. The present invention can also evaluate surface coatings, such as thermal control coatings, laminated surface integrities, and the effects of damage from both mechanical and radiation events, all of which can be characterized by the ability to transfer heat. The present invention can also measure changes caused by ion implantation, ion diffusion, etching, oxidation, ultraviolet degradation, physical impact, and other processes that change the thermal properties of the model.

As can be appreciated, the present invention measures rates of heat transfer remotely and without contact of the model. The present invention can determine flow characteristics as a function of position on the model and thereby form an image of the flow across the entire model. In addition, the model does not have to be altered with holes, wires, or tubes. Although surface coatings are not necessary, surface coatings may be used to maximize the efficiency of the present invention in view of the particular material out of which the model is constructed.

The above describes only a limited number of embodiments of the present invention and it is contemplated that various modifications thereto may be made but nevertheless come within the scope of the present invention as defined by the claims.

What is claimed is:

1. A method of characterizing a flow over a sample, comprising the steps of:
   remotely imparting a known total of thermal energy from a thermal energy source remote from said flow to a measurement surface area on said sample without the sample being in physical contact with said thermal energy source;
   remotely sensing the thermal energy imparted to said sample from said remote thermal energy source and radiated from said measurement surface area of said sample; and
   remotely determining a rate of change in heat over said measurement area of the sample from said radiated and remotely sensed thermal energy.

2. The invention of claim 1 further including the step of comparing the rate of change in heat with a reference characterization.

3. The invention of claim 1 wherein the step of imparting thermal energy includes the step of providing the thermal energy source remotely from the flow.

4. The invention of claim 1 wherein the step of determining the rate of change in heat includes the step of measuring a heat loss from the sample.

5. The invention of claim 1 wherein the step of determining the rate of change in heat includes the step of integrating a plurality of measured heat losses.

6. A method of characterizing a flow in a wind tunnel, comprising the steps of:
   non-invasively imparting a known total of thermal energy to a sample in the wind tunnel from a remote source;
   remotely receiving thermal energy imparted to said sample from said remote source and radiated from at least one measurement area on said surface of said sample;
   remotely measuring any changes in said radiated and received thermal energy and integrating said received thermal radiations; and
   comparing the measured changes in said radiated thermal energy with a reference characterization.

7. The invention of claim 6 wherein the step of measuring the changes in thermal radiations includes the step of measuring an amount of heat transferred to the flow in said wind tunnel from said measurement area on said surface of said sample.

8. The invention of claim 6 wherein the step of integrating the thermal radiations includes the step of producing a temperature distribution curve.

9. The invention of claim 8 wherein the step of comparing the changes in thermal radiations from said measurement area includes the step of performing a curve-fitting function on the temperature distribution curve both spatially and temporally.

10. The invention of claim 9 wherein the step of comparing the changes in thermal radiations includes the step of comparing a temperature fit with the reference characterization.

11. The invention of claim 6 wherein the step of imparting thermal energy includes the step of providing one of a pulsed thermal energy form, a continuous thermal energy form, a modulated amplitude energy form, and a frequency modulated energy form.

12. A method for characterizing a flow in a wind tunnel, comprising the steps of:
   non-invasively imparting thermal energy to a sample in the wind tunnel;
   remotely receiving thermal radiations from at least one measurement area on said surface of said sample, wherein the sample includes a thermal insulator coating over said measurement area and a thermal energy absorbing coating over said insulator coating for absorbing a portion of said thermal energy imparted thereto;

measuring any changes in said thermal radiations; and comparing the changes in said thermal radiations with a reference characterization.

13. A system for characterizing a flow over a sample in a wind tunnel by remotely, non-invasively, and passively measuring thermal characteristics of the sample, comprising:

means for remotely and non-invasively imparting thermal energy to the sample;

means for focusing the thermal energy onto the sample, the focusing means being intermediate the imparting means and the sample;

means for receiving thermal radiations over a period of time from a plurality of selected measurement areas on the surface of said sample, the receiving means being in remote thermal communication with the sample and capable of producing signals indicative of said thermal radiations; and means for analyzing said signals to determine the rate of change of thermal radiations from said selected measurement areas on the surface of said sample.

14. The invention of claim 13 further including means for scanning in two orthogonal angles the thermal energy from the imparting means.

15. The invention of claim 14 including means for improving a signal-to-noise ratio.

16. The invention of claim 15 further including means for curve-fitting a temperature distribution curve which is created from the signals, such curve-fitting being one of spatially, temporally, and both spatially and temporally.

17. The invention of claim 13 further including means for scanning the imparting thermal energy into a thermal pattern.

18. The invention of claim 11 wherein the thermal radiation pattern is selected from the group consisting of a line, a series of spots a grid, and a locus of points.

19. The invention of claim 18 wherein the thermal radiation pattern is varied in both a time and a space parameter.

20. The invention of claim 13 wherein the means for imparting thermal energy is selected from an energy source selected from the group consisting of a pulsed laser, a continuous laser, and a modulated laser.

21. The invention of claim 20 wherein the imparting thermal energy is in a modulated form and the signals are scanned to extract a phase and amplitude picture of radiating thermal energy.

* * * * *